United States Patent

O'Callaghan et al.

[11] 4,385,054
[45] May 24, 1983

[54] 1-ACETOXYETHYL-3-(2-CHLOROETHYL-CARBAMOYLOXYMETHYL)-7-[2-(FUR-2-YL)-2-METHOXYIMINOACETAMIDO]-CEPH-3-EM-4-CARBOXYLATE

[75] Inventors: Cynthia H. O'Callaghan, Gerrards Cross; Michael Gregson, Greenford, both of England

[73] Assignee: Glaxo Group Limited, London, England

[21] Appl. No.: 259,363

[22] Filed: Apr. 30, 1981

Related U.S. Application Data

[63] Continuation of Ser. No. 48,783, Jun. 15, 1979, abandoned, which is a continuation of Ser. No. 931,265, Aug. 4, 1978, abandoned.

[30] Foreign Application Priority Data

Aug. 12, 1977 [GB] United Kingdom ............... 34041/77

[51] Int. Cl.³ .................. A61K 31/545; C07D 501/34
[52] U.S. Cl. ....................................... 424/246; 544/22
[58] Field of Search ........................... 544/22; 424/246

[56] References Cited

U.S. PATENT DOCUMENTS

| 3,962,227 | 6/1976 | Chauvette | 544/22 |
| 3,971,778 | 7/1976 | Cook et al. | 544/22 |
| 3,974,153 | 8/1976 | Cook et al. | 544/22 |
| 4,011,215 | 3/1977 | Cook et al. | 544/28 |
| 4,103,084 | 7/1978 | Bradshaw et al. | 544/22 |
| 4,122,259 | 10/1978 | Humber | 544/22 |
| 4,162,360 | 7/1979 | Bradshaw et al. | 544/22 |
| 4,267,320 | 5/1981 | Gregson et al. | 544/22 |

FOREIGN PATENT DOCUMENTS 2405877  8/1974  Fed. Rep. of Germany .

Primary Examiner—Paul M. Coughlan, Jr.
Attorney, Agent, or Firm—Bacon & Thomas

[57] ABSTRACT

Compounds of the general formula

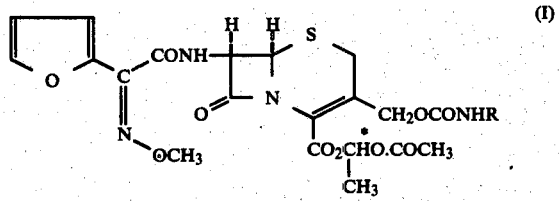

(wherein R represents a methyl or 2-chloroethyl group and * represents an asymmetric carbon atom). The above compounds are useful as orally administrable antibiotics.

2 Claims, No Drawings

1-ACETOXYETHYL-3-(2-CHLOROETHYLCAR-BAMOYLOXYMETHYL)-7-[2-(FUR-2-YL)-2-METHOXYIMINOACETAMIDO]CEPH-3-EM-4-CARBOXYLATE

This application is a continuation, of application Ser. No. 048,783, filed June 15, 1979 now abandoned which is a continuation of Ser. No. 931,265 filed Aug. 4, 1978 now abandoned.

This invention is concerned with improvements in or relating to cephalosporin antibiotics. More particularly the invention is concerned with a biologically acceptable ester derivative of respectively (6R,7R)-3-N-methylcarbamoyloxymethyl-7-[(Z)-2-(fur-2-yl)-2-methoxyiminoacetamido]ceph-3-em-4-carboxylic acid (i.e. the syn isomer) and the corresponding 3-N-(2-chloroethyl)-carbamoyloxymethyl analogue.

(6R,7R)-3-N-Methyl-carbamoyloxymethyl-7-[(Z)-2-(fur-2-yl)-2-methoxyimino acetamido]ceph-3-cm-4-carboxylic acid and its 3-N-(2-chloroethyl)-carbamoyloxymethyl analogue, as described respectively in Belgian Patent Specification Nos. 832651 and 832435, are valuable broad spectrum antibiotics which are stable in the presence of human serum and which also show high stability to β-lactamases produced by a variety of organisms.

These compounds are principally of value as injectable antibiotics since they are poorly absorbed from the gastro-intestinal tract and are therefore present in sera and urine only in low concentrations after oral administration. We have accordingly investigated the possible activity upon oral administration of various derivatives of such compounds since the development of derivatives which are absorbed through the gastro-intestinal tract and exhibit good antibacterial activity following oral administration would extend still further the valuable therapeutic potential of the parent compounds.

It is known from the literature pertaining to β-lactam antibiotics that the absorption from the gastro-intestinal tract following oral administration of certain penicillin and cephalosporin antibiotics may be improved (compared with the parent antibiotic) by converting the free 3-carboxy group in the case of penicillin compounds or the free 4-carboxy group in the case of cephalosporin compounds, to particular esterified carboxy groups. Thus, for example, penicillin G may be converted into its acetoxymethyl ester to provide a compound having improved absorption from the gastro-intestinal tract after oral administration, compared with penicillin G itself. It is believed that the presence of an appropriate esterifying group enhances absorption of the parent antibiotic from the gastro-intestinal tract, the esterifying group being hydrolysed, after absorption by enzymes present in, for example, serum and body tissues to yield the antibiotically active parent acid. It will be appreciated that the precise nature of the esterifying group is critical since it is necessary that the ester should be sufficiently stable to allow the ester to reach the site of absorption without undergoing significant degradation, e.g. in the stomach, while on the other hand the ester must be sufficiently susceptible for conversion to the antibiotically active parent acid within a short time of the ester being absorbed.

Moreover, the extent to which the particular ester group enhances the oral absorption of the β-lactam antibiotic is random and unpredictable and depends upon the nature of the parent acid selected. For example, an esterifying group which has been found to be effective in improving the usefulness of a penicillin antibiotic does not necessarily convey similar advantages to an antibiotic of the cephalosporin series, and inconsistencies are noted within each of these particular series of β-lactam antibiotics.

We have now found that the acetoxyethyl esters of the above ceph-3-em-4-carboxylic acid, which may be represented by the formula

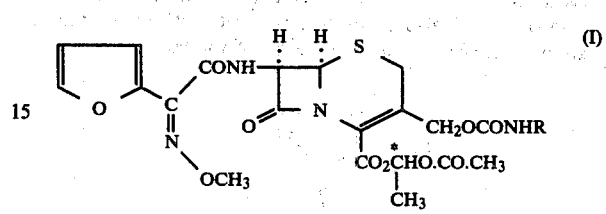

(wherein R represents a methyl or 2-chloroethyl group and the asterisk denotes an asymmetric carbon atom) possess properties which render these compunds of significant potential value as orally administrable antibiotics. The individual diastereoisomers, as well as mixtures thereof, are embraced by the invention.

The esters of formula I possess reasonable stability as evidenced by the fact that they exhibit low antibacterial activity in vitro compared to the parent acids (this indicates that a high proportion of ester remains unchanged throughout the in vitro tests and so confirms the stability of the esters).

In vivo testing in rats confirms that oral administration of the esters of formula (I) leads to significantly greater absorption of the parent carboxylic acids as evidenced by increased urinary recovery, then does oral administration of the parent carboxylic acids themselves.

The esters of formula (I) may be prepared in conventional manner, for example, by a process as described below.

Thus, according to a preferred feature of the present invention we provide a process for the preparation of a compound of formula I (as hereinbefore defined) which comprises (A) reacting a compound of formula

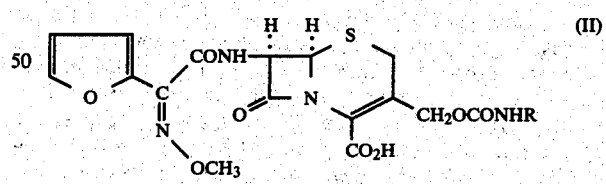

(wherein R is as defined above) or a salt thereof (e.g. an alkali metal salt such as the sodium or potassium salt or an onium salt, e.g. an ammonium salt for example a quaternary ammonium salt) with a haloester of formula

(wherein X is halogen such as chlorine, bromine or iodine); (B) acylating a compound of formula

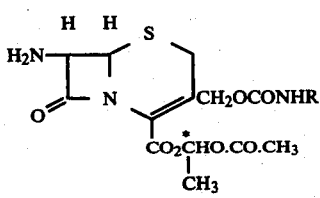

(wherein R is as hereinbefore defined) or an acid addition salt or N-silyl derivative thereof, with an acylating agent corresponding to the acid of formula

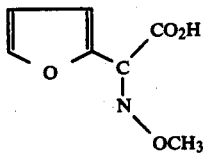

or (C) carbamoylating a compound of formula

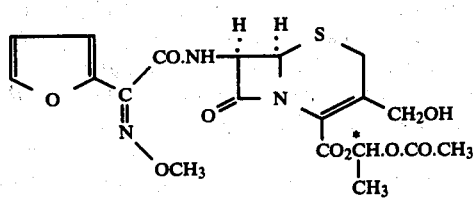

The reaction of the parent carboxylic acid of formula (II) with the haloester of formula (III) is conveniently effected in solution in an inert organic solvent (e.g. an N,N-disubstituted amide such as N,N-dimethylformamide or N,N-dimethylacetamide; a ketone such as acetone; a sulphoxide such as dimethylsulphoxide; a nitrile such as acetonitrile; hexamethylphoshoric triamide; or liquid sulphur dioxide) at a temperature in the range $-50°$ to $+150°$ C. e.g. $-10°$ to $+50°$ C. conveniently between $-10°$ C. and room temperature. When the parent carboxylic acid is employed in the form of a salt, for example, the potassium salt, and the reaction is effected in an organic solvent, e.g. in a nitrile solvent, a crown ether such as 18-crown-6 may, if desired be employed. When the parent carboxylic acid is employed as starting material it may be advantageous to effect the reaction in the presence of a base, e.g. a weak inorganic base such as sodium carbonate or potassium carbonate; it is convenient to add the base to the cephalosporin-containing reaction system prior to addition of the haloester (III). The use of potassium carbonate as base in conjunction with a compound (III) in which X is bromine or iodine has been found advantageous in that under these conditions the formation of a ceph-2-em ester product is kept to a minimum. It is convenient to employ substantially equivalent amounts of ceph-3-em-4-carboxylic acid and base, e.g. about 0.5 moles of a diacidic base such as potassium carbonate per mole of carboxylic acid. The haloester (III) is conveniently employed in slight excess, e.g. in an amount of 1–1.5 moles per mole of carboxylic acid.

The course of the reaction may readily be monitored by t.l.c., since the process involves conversion of a polar acid or salt starting material to a neutral ester product.

The compounds of formula (I) may conveniently be prepared by acylating a compound of formula (IV) with an acylating agent comprising an acid halide, particularly an acid chloride or bromide of the said acid. Such acylation may be effected at temperatures of from $-50°$ to $+50°$ C., preferably $-20°$ to $+30°$ C. The acylation may be effected in aqueous or non-aqueous media.

Acylation with an acid halide may be effected in the presence of an acid binding agent (e.g. a tertiary amine such as triethylamine or N,N-dimethylaniline, an inorganic base such as calcium carbonate or sodium bicarbonate, or an oxirane, preferably a lower-1,2-alkylene oxide such as ethylene oxide or D, L-2-methyloxirane which serves to bind hydrogen halide liberated in the acylation reaction.

The free acid of formula (V) may itself be used as the acylating agent. Such acylations are desirably conducted in the presence of, for example, a carbodiimide such as N,N′-dicyclohexylcarbodiimide; a carbonyl compound such as carbonyldiimidazole; or an isoxazolinium salt such as N-ethyl-5-phenylisoxazolinium-3′-sulphonate or N-t-butyl-5-methylisoxazolinium perchlorate. The condensation reaction is desirably effected in an anhydrous reaction medium, e.g. methylene chloride, dimethylformamide or acetonitrile.

Acylation may also be effected with other amide-forming derivatives of the free acid such as, for example, a symmetrical anhydride or a mixed anhydride, e.g. with pivalic acid or formed with a haloformate such as a lower alkyl haloformate. The mixed or symmetrical anhydrides may be generated in situ. Thus, for example, a mixed anhydride may be generated using N-ethoxycarbonyl-2-ethoxy-1,2-dihydroquinoline. Mixed anhydrides may also be formed with phosphorus acids (for example phosphoric or phosphorous acids), sulphuric acid or aliphatic or aromatic sulphonic acids (for example p-toluene-sulphonic acid).

The above-described starting materials of formula (IV) may be prepared in conventional manner, for example, using the techniques described in U.S. Pat. No. 3,905,963 and British Patent Specifications Nos. 1,041,985 and 1,350,772.

The carbamoylation of the compound of formula (VI) may be effected for example, in an analogous manner to that described in the said Belgian Patent Specification Nos. 832651 and 832435.

If the desired ester product is significantly contaminated by the corresponding ceph-2-em isomer the product may be oxidised (e.g. by treatment with a peracid such as metaperiodic acid, peracetic acid, monoperphthalic acid or m-chloroperbenzoic acid or with t-butyl hypochlorite in the presence of a weak base such as pyridine) to give the ceph-3-em 1-oxide ester, which may then be reduced (e.g. by treatment with acetyl chloride and potassium iodide) to yield the substantially pure ceph-3-em ester.

The individual diastereoisomers may be isolated by recrystallization from the isomeric mixture.

The esters of formula I are useful for treating a variety of diseases caused by pathogenic bacteria in human beings and animals such as respiratory tract and urinary tract infections.

The esters of formula I may be formulated as compositions for oral administration in conventional manner, with the aid of any necessary pharmaceutical carriers or excipients. The compositions are conveniently prepared as tablets, capsules or sachets, advantageously in unit dose form, and may contain conventional excipients such as binding agents, fillers, lubricants, disintegrants and wetting agents. Tablets may be coated in conventional manner. The active compounds may further be formulated in rectal compositions such as suppositories or retention enemas.

The compositions may contain from 0.1% upwards, e.g. 0.1–99%. conveniently from 10–60% of the active ingredient (I), depending on the method of administration. Compositions in dosage unit form conveniently contain 50–500 mg of the active ingredient (calculated as the parent ceph-3-em-4-carboxylic acid). Doses employed for adult human treatment will typically be in the range 500–5000 mg, per day, e.g. 1500 mg per day, (calculated as the parent ceph-3-em-4-carboxylic acid) although the precise dose will depend on, inter alia, the frequency of administration.

The following Examples illustrate the present invention. All temperatures quoted are in °C. Melting points were determined in capillaries and are uncorrected. They were measured on a Mettler apparatus and take the form ($M_y{}^x$) where x is the rate of heating (in °C. per minute) and y is the insertion temperature. T.l.c. is thin layer chromatography using pre-coated plates (Merck $F_{254}$, 0.25 mm thick coating) which were examined under ultra-violet light at 254 nm and were developed by spraying with a solution of ninhydrin in n-butanol and heating to ca 140°. N,N-Dimethylformamide was dried by passage through a column of acidic alumina.

The following Examples 1 and 2 illustrate the preparation of compounds according to the invention.

EXAMPLE 1

(R and S)-1-Acetoxyethyl (6R,7R)-3-N-methylcarbamoyloxymethyl-7-[(Z)-2-(fur-2-yl)-2-methoxyiminoacetamido]ceph-3-em-4-carboxylate A solution of (6R,7R)-3-N-methylcarbamoyloxymethyl-7-[(Z)-2-(fur-2-yl)-2-methoxyiminoacetamido]-ceph-3-em-4-carboxylic acid (0.682 g, 1.56 mmole) in N,N dimethylformamide (10 ml) was successively treated at 0° with dry potassium carbonate (0.107 g, 0.78 mmole) and a solution of (R,S)-1-acetoxyethyl bromide (0.286 g, 1.71 mmole) in N,N dimethylformamide (5 ml). The reaction mixture was stirred at 0° for 50 minutes and partitioned between ethyl acetate (40 ml) and 2-N hydrochloric acid (40 ml). The aqueous phase was extracted with more ethyl acetate (40 ml) and the combined organic extracts were washed successively with water (40 ml), aqueous sodium bicarbonate solution (40 ml), water (40 ml), saturated brine (40 ml) and dried (magnesium sulphate) and evaporated to dryness in vacuo. Trituration of the residue (0.63 g) with anhydrous ether afforded the title ester (0.45 g) as a solid, $[\alpha]_D+49.6°$ (c, 1.07, DMSO), $\nu_{max}$ (Nujol) 3500 to 3100 (2×NH), 1790 (β-lactam), 1766 (O.CO.CH$_3$), 1725 (CO$_2$R), 1680 (O.CO.NHCH$_3$) and 1680 and 1534 cm$^{-1}$ (CONH).

EXAMPLE 2

(R and S)-1-Acetoxyethyl (6R,7R)-3-(2-chloroethylcarbamoyloxymethyl)-7-[(Z)-2-(fur-2-yl)-2-methoxyiminoacetamido]-ceph-3-em-4-carboxylate (a) (R and S)-1-Acetoxyethyl (6R,7R)-3-(2-chloroethylcarbamoyloxymethyl)-7-[(Z)-2-(fur-2yl)-2-methoxyiminoacetamido]-ceph-2- and 3-em-4-carboxylate A solution of (6R,7R)-3-(2-chloroethylcarbamoyloxymethyl)-7-[(Z)-2-(fur-2-yl)-2-methoxyiminoacetamido]ceph-3-em-4-carboxylic acid (1.336 g, 2.74 mmole) in N,N dimethylformamide (15 ml) was treated with finely ground potassium carbonate (0.190 g, 1.37 mmole) and the mixture stirred for 10 min, by which time the solid had almost completely dissolved. (R,S)-1-Acetoxyethyl bromide (0.70 g, 4.2 mmole) was added and the reaction was stirred at 21° for 75 mins. The reaction mixture was partitioned between ethyl acetate (100 ml) and 2 N-hydrochloric acid (100 ml). The aqueous layer was extracted with further ethyl acetate (2×100 ml) and the combined organic extracts were successively washed with 2 N-hydrochloric acid (150 ml), water (2×150 ml), 3% aqueous sodium bicarbonate solution (2×150 ml), water (3×150 ml) and saturated sodium chloride solution (150 ml). The solution was dried and the solvent removed in vacuo to give the crude product as a yellow viscous oil (1.390 g).

(b) (R and S)-1-Acetoxyethyl (1S,6R,7R)-3-(2-chloroethylcarbamoyloxymethyl)-7-[(Z)-2-(fur-2-yl)-2-methoxyiminoacetamido]-ceph-3-em-4-carboxylate, 1-oxide The crude sulphide from the previous stage (1.390 g), in dichloromethane (7 ml) was treated with a solution of m-chloroperbenzoic acid (0.48 g, 2.8 mmol) in dichloromethane (8 ml). The reaction mixture was stirred for 20 minutes, when t.l.c. showed reaction was complete. The solvent was evaporated in vacuo and the residue was triturated with ether (80 ml) to give the title oxide as a white solid (1.335 g), m.p. ($M_{80}{}^2$) 149° (dec), $[\alpha]_D+48°$ (c 0.44, DMSO).

(c) (R and S)-1-Acetoxyethyl (6R,7R)-3-(2-chloroethylcarbamoyloxymethyl)-7-[(Z)-2-(fur-2-yl)-2-methoxyiminoacetamido]ceph-3-em-4-carboxylate A solution of (R and S)-1-acetoxyethyl (1S,6R,7R)-3-(2-chloroethylcarbamoyloxymethyl)-7-[(Z)-2-(fur-2-yl)-2-methoxyiminoacetamido]ceph-3-em-4-carboxylate, 1-oxide (0.885 g, 1.5 mmol) in N,N-dimethylformamide (10 ml) was cooled to 0° and treated with potassium iodide (1.0 g, 6.0 mmol) followed by acetyl chloride (0.22 ml, 0.24 g, 3.0 mmol). The reaction was stirred at 0° for 1.5 hours, when t.l.c. indicated that reduction was complete. The reaction mixture was partitioned between ethyl acetate (100 ml) and 2 N-hydrochloric acid (100 ml) and the aqueous layer was extracted with further ethyl acetate (2×100 ml). The combined organic extracts were washed successively with 2 N-hydrochloric acid (150 ml), water (2×150 ml) sodium metabisulphite solution (150 ml), water (4×150 ml) and saturated sodium chloride solution (150 ml). The solution was dried (MgSO$_4$) and the solvent was removed in vacuo to give a yellow froth which was triturated with ether (40 ml) to give the title ester as a buff solid (0.429 g), m.p. ($M_{80}{}^2$) 103.5° (with decomposition), $[\alpha]_D+20°$ (c 0.53, DMSO).

The following Examples A to D illustrate pharmaceutical compositions according to the invention.

EXAMPLE A

| Tablets | Per Tablet |
| --- | --- |
| Densified (R and S)-1-Acetoxyethyl (6R, 7R)-3-N—methylcarbamoyloxymethyl-7-[(Z)-2-(fur-2-yl)-2 methoxyiminoacetamido]ceph-3-em-4-carboxylate, as acid with 1% magnesium stearate | 303.70 mg |

-continued

| Tablets | Per Tablet |
|---|---|
| Sodium starch glycolate | 9.00 mg |
| Sodium lauryl sulphate | 4.50 mg |
| Microcrystalline cellulose, sufficient to tablet core compression weight | 450.00 mg |

Method

Blend the antibiotic with magnesium stearate in a blender, and compress into 'slugs' using a heavy duty tableting machine. Pass the slugs through a series of sieves (10, 12, 16 or 20 mesh) to obtain free flowing granules. Alternatively a roller compactor may be used for densification of the antibiotic. Add the remaining ingredients to the granules and blend thoroughly in a suitable blending equipment and compress using normal or deep concave punches into tablets of appropriate diameter (9–12 mm).

Film coat the tablets (if required using an aqueous or nonaqueous solution of cellulosic material with plasticizers. A colour may also be added to the coating solution.

EXAMPLE B

| Tablets | Per Tablet |
|---|---|
| (R and S)-1-Acetoxyethyl (6R, 7R)-3-N—methylcarbamoyloxymethyl-7-[(Z)-2-(fur-2-yl)-2-methoxyimino acetamido]ceph-3-em-4-carboxylate as acid | 300.70 mg |
| Maize starch | 22.50 mg |
| Sodium starch glycolate | 9.00 mg |
| Sodium lauryl sulphate | 4.50 mg |
| Magnesium stearate | 4.50 mg |
| Microcrystalline cellulose, sufficient to tablet core compression weight | 450.0 mg |

Method

Prepare a 10% starch paste and add to the antibiotic to produce a wet mass suitable for granulation. Prepare the granules using a suitable mixer. Dry the granules in a tray or fluid bed dryer. Mix the remaining ingredients and compress and if necessary film coat the tablet cores as described in Example A.

EXAMPLE C

| Capsules | Per Capsule |
|---|---|
| Densified (R and S)-1-Acetoxyethyl (6R, 7R)-3-N—methylcarbamoyloxymethyl-7-[(Z)-2-(fur-2-yl)-2-methoxyiminoacetamido]-ceph-3-em-4-carboxylate as acid with 1% magnesium stearate | 303.70 mg |
| Sodium starch glycolate | 6.00 mg |
| Finely divided silicon dioxide | 3.00 mg |
| | 312.70 mg |

Method

Prepare free flowing granules of the densified antibiotic as described in Example A, mix the remaining ingredients using blending equipment and fill in appropriate size (0 or 1) two-piece locking capsules on an automatic capsule filling machine.

EXAMPLE D

| Powder for Oral Suspension | Per Sachet |
|---|---|
| (R and S)-1-Acetoxyethyl (6R, 7R)-3-N—methylcarbamoyloxymethyl-7-[(Z)-2-(fur-2-yl)-2-methoxyimino-acetamido]ceph-3-em-4-carboxylate, as acid | 250 mg |
| Sodium carboxymethyl cellulose (low viscosity) | 90 mg |
| Sunset yellow | 5 mg |
| Spray-dried orange flavour | 150 mg |
| Caster sugar | 2.2 g |

Method

Blend the milled ester intimately with the sodium carboxymethyl cellulose, the flavour and the colour. Blend this further with the caster sugar adding the latter in two stages. Transfer the required weight to a paper-/aluminium/polythene sachet and seal by heat.

The contents of each sachet are intended for constitution in about 15 ml of water, shortly before administration.

We claim:

1. (R and S)-1-Acetoxyethyl (6R,7R)-3-(2-chloroethylcarbamoyloxymethyl)-7-[(Z)-2-(fur-2-yl)-2-methoxyiminoacetamido]ceph-3-em-4-carboxylate.

2. Pharmaceutical compositions comprising, as active ingredient, an antibacterial effective amount of the compound of claim 1 in association with at least one pharmaceutical carrier or excipient.

* * * * *